(12) United States Patent
Kraft et al.

(10) Patent No.: US 7,482,605 B2
(45) Date of Patent: Jan. 27, 2009

(54) ENERGY FILTER DEVICE

(75) Inventors: Gerhard Kraft, Darmstadt (DE); Ulrich Weber, Bad Homburg (DE); Sebastian Kraft, Tübingen (DE); Stephan Kraft, Dossenheim (DE)

(73) Assignee: GSI Helmholtzzentrum Für Schwerionenforschung GmgH (DE)

( * ) Notice: Subject to any disclaimer, the term of this patent is extended or adjusted under 35 U.S.C. 154(b) by 521 days.

(21) Appl. No.: 10/853,850

(22) Filed: May 25, 2004

(65) Prior Publication Data

US 2005/0029471 A1    Feb. 10, 2005

(30) Foreign Application Priority Data

May 26, 2003    (DE)    ............... 103 23 654

(51) Int. Cl.
*H01J 49/44* (2006.01)
*A61N 5/10* (2006.01)

(52) U.S. Cl. ............... 250/492.3; 250/493.1; 378/147; 378/152

(58) Field of Classification Search ........... 250/396 ML
See application file for complete search history.

(56) References Cited

U.S. PATENT DOCUMENTS

| | | | | |
|---|---|---|---|---|
| 4,672,212 | A * | 6/1987 | Brahme ............... | 250/505.1 |
| 4,845,371 | A * | 7/1989 | Stieber ............... | 250/505.1 |
| 5,440,133 | A | 8/1995 | Moyers et al. ........ | 250/492.3 |
| 6,118,854 | A * | 9/2000 | Solomon et al. ...... | 378/156 |
| 6,316,776 | B1 * | 11/2001 | Hiramoto et al. ..... | 250/492.3 |
| 6,355,383 | B1 * | 3/2002 | Yamashita ........... | 430/5 |
| 6,617,598 | B1 * | 9/2003 | Matsuda ............. | 250/492.3 |
| 6,683,320 | B2 * | 1/2004 | Gerlach et al. ....... | 250/494.1 |
| 6,924,493 | B1 * | 8/2005 | Leung ............... | 250/492.21 |
| 2002/0162774 | A1 | 11/2002 | Scheidemann et al. .. | 209/213 |

FOREIGN PATENT DOCUMENTS

| | | |
|---|---|---|
| DE | 37 05 295 | 9/1988 |
| DE | 3705395 | 9/1988 |
| DE | 101 40 100 | 3/2002 |
| DE | 10140100 | 3/2002 |
| GB | 2 202 420 | 9/1998 |
| GB | 2 370 746 | 7/2002 |
| JP | 6-154351 | 6/1994 |
| JP | 06-154351 | 6/1994 |

(Continued)

OTHER PUBLICATIONS

R.A. Snavely et al. "Intense High-Energy Proton Beams from Petawatt-Laser Irradiation of Solids" (2000) *Phys. Rev.* Lett. vol. 85, pp. 2945-2948.

(Continued)

*Primary Examiner*—David A. Vanore
(74) *Attorney, Agent, or Firm*—Ostrolenk, Faber, Gerb & Soffen, LLP

(57) ABSTRACT

An energy filter device for beams which are used in the course of ion beam therapy, wherein at least one passive modulator is provided. The modulator can comprise a scattering film for the beams and a collimator with an opening for controlling the beams, or a magnetic filter and an absorber, or a nonlinear filter and an apparatus for clipping the intensity of individual energy levels of the beams.

18 Claims, 4 Drawing Sheets

FOREIGN PATENT DOCUMENTS

| | | |
|---|---|---|
| JP | 11-28252 | 2/1999 |
| JP | 11-028252 | 2/1999 |
| WO | WO 00/49624 | 8/2000 |
| WO | WO 01/33764 | 4/2002 |
| WO | WO 02/33764 | 4/2002 |

OTHER PUBLICATIONS

C.M. Ma et al. "Laser Accelerated Proton Beams for Radiation Therapy" (2001) *Med. Phys.* vol. 28, p. 1236.

E. Fourkal et al. "Particle in cell simulation of laser-accelerated proton beams for radiation therapy" (2002) *Med. Phys.* vol. 29 pp. 2788-2798.

International Search Report dated Sep. 22, 2006.

XP-002397156.

E. Fourkal, et al., Particle in cell simulation of laser-accelerated proton beams for radiation therapy, Med. Phys. 29 (12), Dec. 2002, pp. 2788-2798.

Anders Gustafsson, et al., A generalized pencil beam algorithm for optimization of radiation therapy, Medical Physics 21(1994) March, No. 3, pp. 343-356.

Goodfellow, "Polymethylmethacrylat", page from German catalogue (2001).

Fourkal, et al., "Particle in cell simulation of laser-accelerated proton beams for radiation therapy", *Med. Phys*, 29(12):2788-2798 (2002).

Gustafsson, "A generalized pencil beam algorithm for optimization of radiation therapy", *Med. Phys.*, 21(3):343-356 (1994).

Jones et al., "Design of a Beam Transport System for a Proton Radiation Therapy Facility", *Proceedings of the 1999 Particle Accelerator Conference*, 2519-2521 (1999).

\* cited by examiner

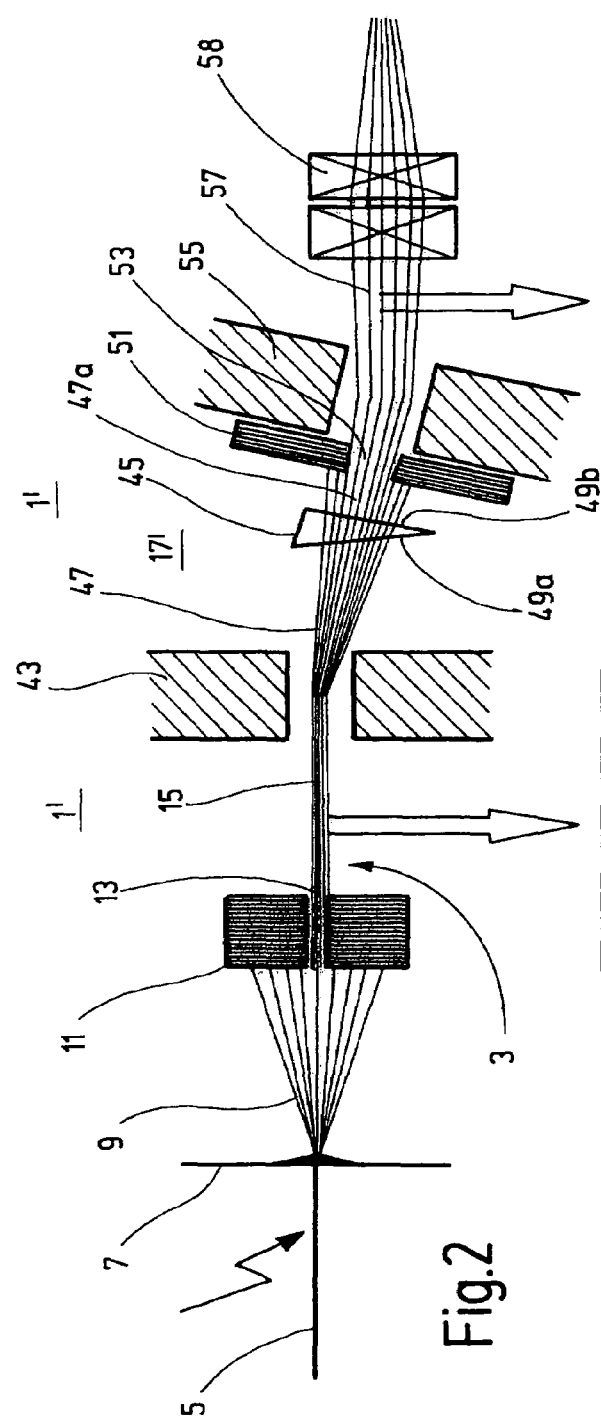
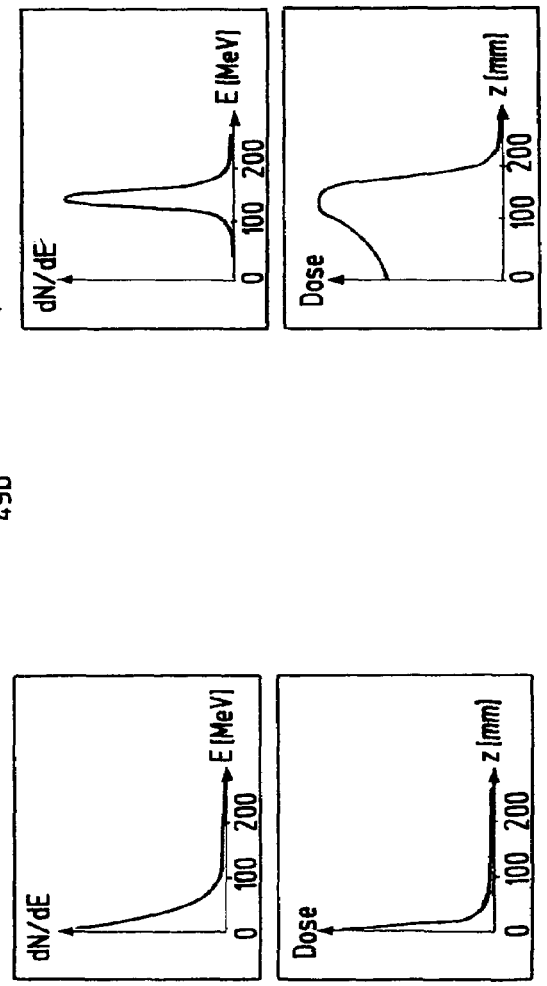
Fig.2
Fig.2a
Fig.2b

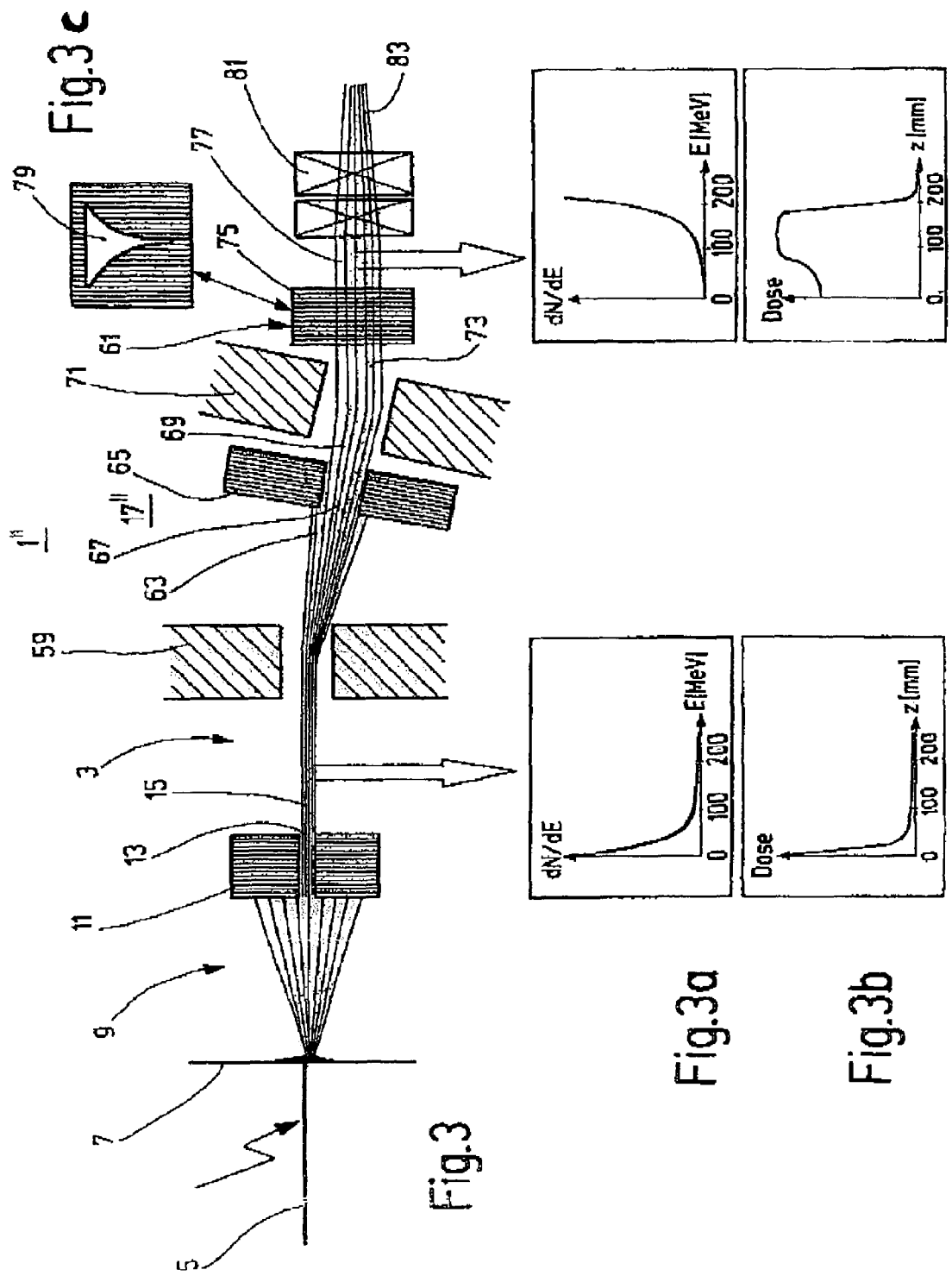

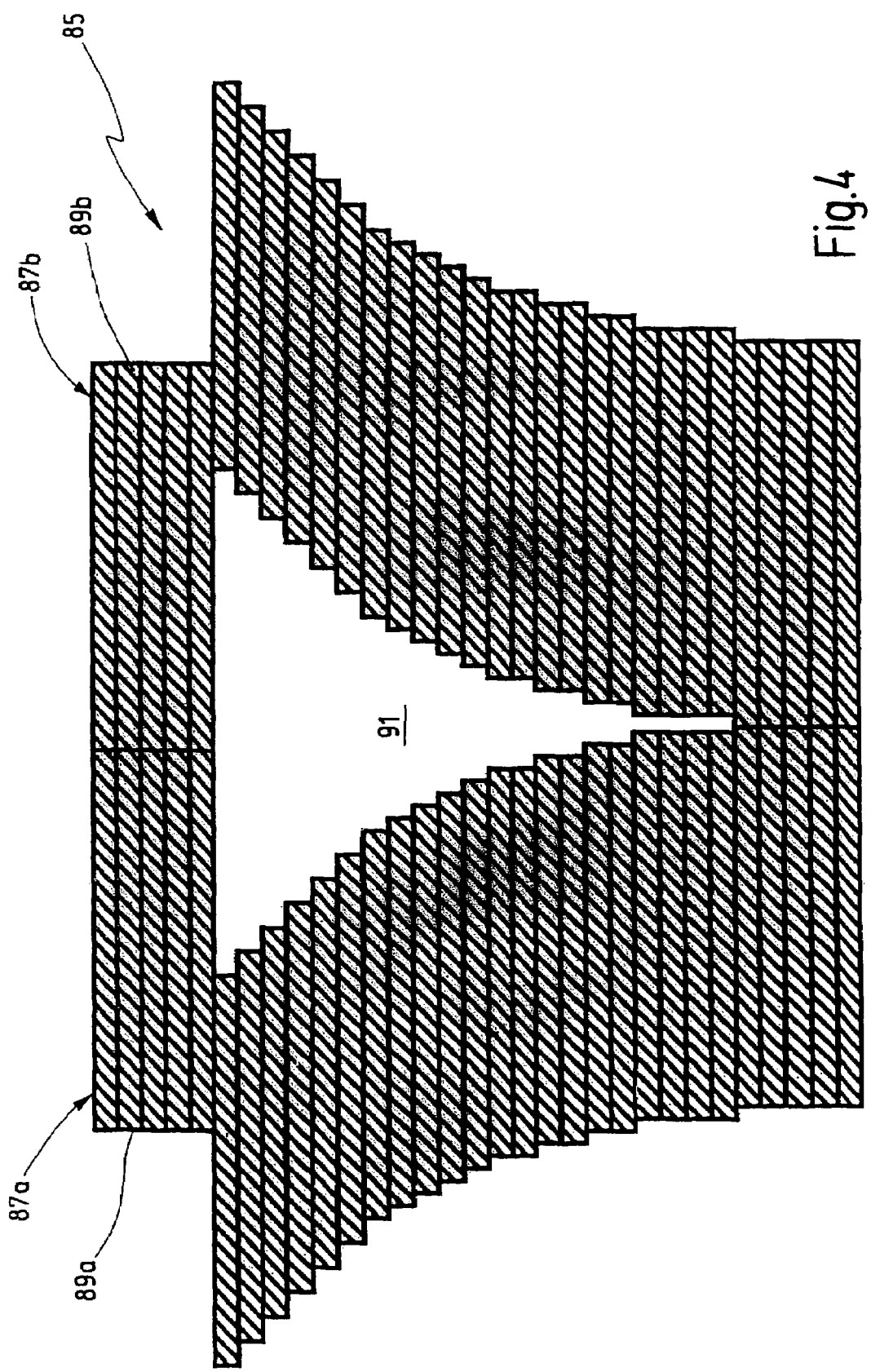

ENERGY FILTER DEVICE

BACKGROUND OF THE INVENTION

The invention relates to an energy filter device for beams used in low beam therapy for controlling the beam intensity and the dose strength of the beam.

Ion beams, that is beams of protons and heavier ions, are used for beam therapy for tumor tissues. Beams of this type have the advantage over photons that they have a considerably better depth dose profile. While, in the case of photon radiation, the dose decreases as the penetration depth increases, it rises slowly in the case of ions and falls away steeply after a sharp maximum, the so-called Bragg peak. The position of this maximum must be distributed accurately over the target volume, in order to concentrate the dose on the tumor and at the same time to reduce the integral dose in the healthy tissue. This also applies to the laser-induced ion beams. Recently, it has been shown that high-intensity, pulsed laser beams can be used to produce relatively tightly focused proton beams from films. However, it has been found that the laser-induced radiation has an energy spectrum which is very poor for cancer therapy, and thus a poor depth dose profile.

The energy spectrum can be improved by masking out a narrow energy band, and destroying the rest of the spectrum, by means of a magnet spectrometer. However, in the case of this selection method, the vast majority of the protons that are produced, specifically more than 95% of them, are filtered out and destroyed without being used.

SUMMARY OF THE INVENTION

The object of the invention is thus to provide an energy filter device by means of which the energy spectrum of laser-induced beams can be utilized better, with fewer protons being filtered out without being used than in the case of conventional magnetic filters.

In order to achieve this object, an energy filter device is proposed which is distinguished by including at least one passive modulator to make it possible to change the energy spectrum of the radiation with a simple device design, such that the energy profile is shifted to higher energy levels, that is it is hardened, and such that a good depth dose profile is produced, which is also referred to as the range profile.

One preferred exemplary embodiment of the energy filter device is distinguished in that the modulator has a scattering film and a collimator, which is arranged at a distance from it. The use of a passive modulator of this type means that the low-energy component of the radiation is lastingly suppressed in comparison to the primary spectrum, and the range profile becomes considerably flatter.

A further preferred exemplary embodiment of the energy filter device is distinguished in that the modulator has a magnetic filter and an absorber.

A further exemplary embodiment of the energy filter device is distinguished in that the modulator has a non-linear filter, by means of which the energy profile and the depth dose profile can be set.

Other features and advantages of the present invention will become apparent from the following description of the invention which refers to the accompanying drawings.

BRIEF DESCRIPTION OF THE DRAWINGS

The invention will be explained in more detail in the following text with reference to the drawings, in which:

FIG. 1a shows the energy spectrum of an ion/proton beam at the various positions in the energy filter device;

FIG. 1b shows the depth dose profile of the beam at various points in the energy filter device;

FIG. 1c shows the scatter of the high-energy and low-energy components of the beam in the energy filter device;

FIG. 2 shows an outline sketch of a further exemplary embodiment of an energy filter device;

FIG. 2a shows the energy spectrum of an ion/proton beam at various positions in the energy filter device;

FIG. 2b shows the depth dose profile of the beam at various points in the energy filter device;

FIG. 3 shows an outline sketch of a further exemplary embodiment of an energy filter device, FIGS. 3a and 3b show the energy spectrum for the embodiment of FIG. 3;

FIG. 3C is a view of the selective collimator of FIG. 3; and

FIG. 4 shows a multi-leaf collimator, seen in the beam direction.

DESCRIPTION OF PREFERRED EMBODIMENTS

Figure 1:
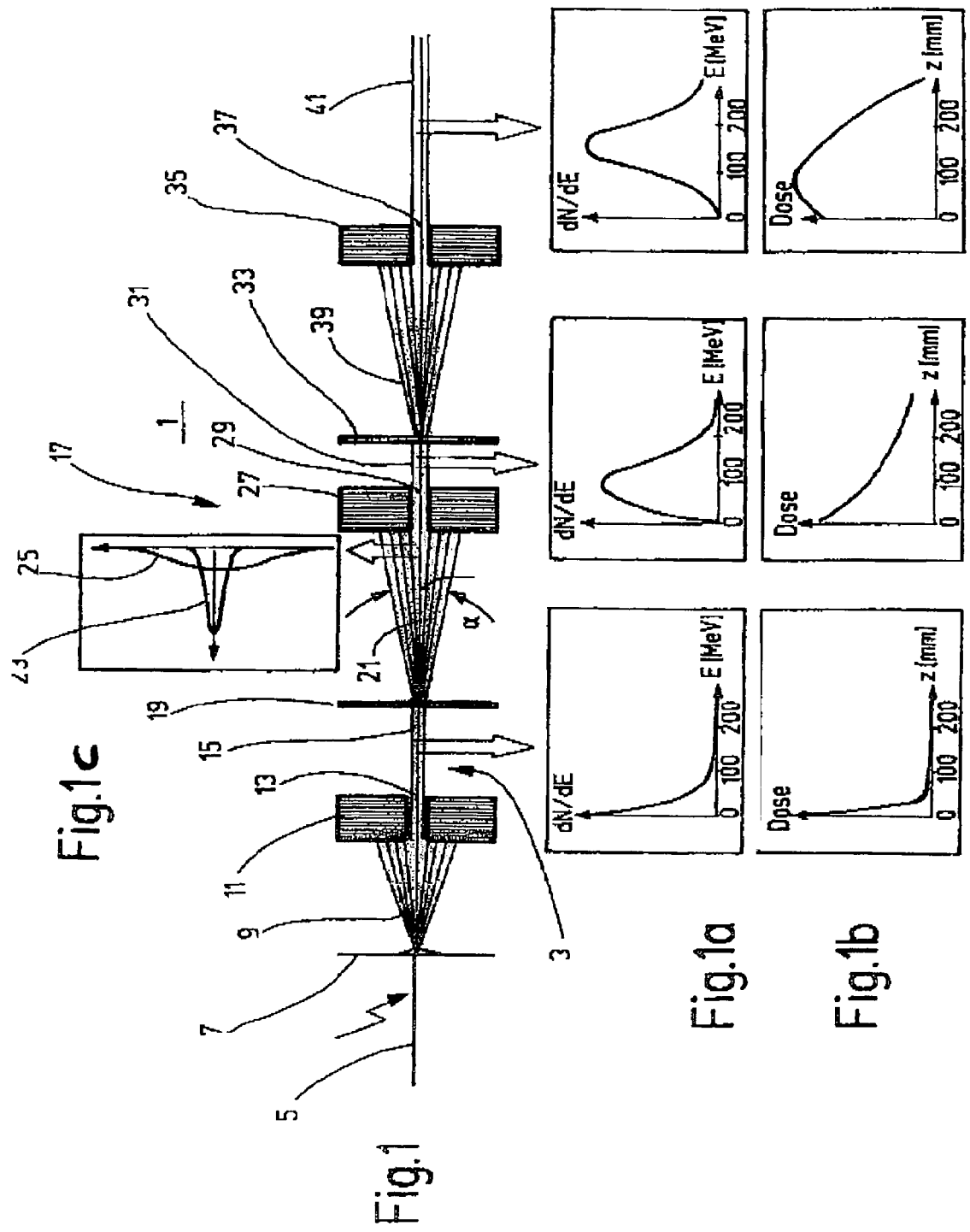
FIG. 1 shows a schematic illustration of an energy filter device.

FIG. 1 shows an ion beam energy filter device, which will be referred to in the following text for short as an energy filter device 1, and through which an ion beam 3 passes. This ion beam 3 is produced by a high-intensity, pulsed laser beam 5, which strikes a target, in this case a converter film 7. Heavy charged particles 9, protons and relatively heavy ions are deposited on this converter film 7. The energy spectrum of the ion radiation made up of these particles 9 cannot be used in practice for radiation therapy, nor can the range profile associated with it.

A first collimator 11 which has a collimator opening 13 is arranged at a distance from the converter film 7, with a collimated beam 15 with a broad spectrum and a strong low-energy component emerging through this collimator opening 13. The outer part of the radiation is masked out by the collimator 11.

The energy spectrum of the beam 15 is shown underneath it, in schematic form, in FIG. 1a. Underneath this, FIG. 1b shows a schematic illustration of the depth dose profile of the beam 15, which has the spectrum illustrated in FIG. 1a.

FIG. 1b shows the beam dose plotted against the penetration depth z (units in millimeters). FIG. 1b clearly shows that the beam dose decreases sharply with the penetration depth.

The collimated beam 15 now strikes the energy filter device 1, which is arranged downstream from the collimator 11, and passes through it from left to right as shown in FIG. 1.

The energy filter device 1 has a passive modulator 17 which, in this exemplary embodiment, is in the form of a scattering filter. This scattering filter has a first scattering film 19 which is arranged, for example, at a distance of 50 cm from the collimator in the beam path, and which the collimated beam 15 strikes. The beam is scattered by the Coulomb interaction. In order to keep the energy loss low, relatively thin scattering films with a thickness, for example, of 5 mm are used, composed, for example, of Plexiglas. The Coulomb interaction results in a Gaussian distribution for the scattering angle α in accordance with the following equation:

$$f(\alpha) = \frac{1}{\sqrt{2\pi}\sigma} \exp - \frac{\alpha^2}{2\sigma^2}$$

where the variance is given by the following relationship:

$$\sigma^2 \approx \frac{1}{E^2}$$

Particles 9 which pass through the first collimator 11 and strike the first scattering film 19 are thus scattered by it, with the scattering becoming greater the lower the energy level of the particles 9.

FIG. 1c shows various distributions for the scattering angle α, with the first curve 23 showing the scattering for the high-energy component of the particles 9 in the scattered beam 21, and the second curve 25 showing the scattering of the low-energy component of the particles.

The energy filter device 1 has a second collimator 27 which is arranged at a distance from the first scattering film 19 and has a collimator opening 29 with a diameter of, for example, 5 mm, through which the majority of the high-energy component of the particles 9 passes, corresponding to the first curve 23, and only a small proportion of the low-energy particles. This results in a beam 31 which is hardened by the collimator, that is to say a beam which has an energy spectrum that is considerably better for radiation therapy than the broadly scattered ion/proton beam which leaves the converter film 7.

Thus, if the second collimator 27 is used to mask out the outer part of the scattered beam 21 after passing through a distance downstream from the first scattering film 19, this results in a transmission filter with a $1/E^2$ characteristic. This is because the collimator which, for example, has a square or round collimator opening clips the beam in two directions.

Underneath the hardened beam 31, FIG. 1a shows the energy spectrum for this beam 31. Underneath this, FIG. 1b shows a schematic illustration of the depth dose profile of the hardened beam 31 with the energy spectrum illustrated in FIG. 1a.

FIG. 1b clearly shows that the depth dose profile of the hardened beam 31 is not the same as that of the collimated beam 15: the beam dose does not fall away so sharply with the penetration depth, and the depth dose profile is thus considerably flatter than that of the collimated beam 15.

The energy filter device 1 that is illustrated in FIG. 1 accordingly has a first hardening stage which comprises the first scattering film 19 and the second collimator 27. However, FIG. 1 also shows that, in the case of the exemplary embodiment of the energy filter device 1 illustrated here, the passive modulator 17 has a second hardening stage, which comprises a second scattering film 33 (which is arranged at a distance from the second collimator 27) and a third collimator 35, which is once again arranged at a distance from the second scattering film 33 and has a collimator opening 37.

The explanation given with regard to the first hardening stage applies in a corresponding manner on passing through the second hardening stage: the hardened beam 31 is scattered by the Coulomb interaction as it passes through the second scattering film 33. A thin scatterer is also used in this case, in order to keep the energy loss low, so that this once again results in the scattering angle α having a Gaussian distribution, as has been described above.

A scattered beam 39 is thus once again produced downstream from the second scattering film 33, and within this beam, the particles with a high energy level have a lower scattering angle than low-energy particles, as has been explained with reference to FIG. 1c.

The outer part of the scattered beam 39 is once again masked out, in the same way as the scattered beam 21, by the third collimator 35, which is arranged downstream from the second scattering film. Considerably more high-energy particles thus emerge through the collimator opening 37 than low-energy particles, thus resulting in a hardened beam 41. The energy spectrum of this beam is shown underneath this beam in FIG. 1a, in this case having a significant maximum, for example, at 200 MeV, and the depth dose profile of this beam with the spectrum as illustrated in FIG. 1a is shown in FIG. 1b.

FIG. 1b clearly shows that the effective dose of the beam increases as the penetration depth increases and falls away after reaching a maximum, for example at a penetration depth of about 100 mm.

The energy filter device 1 shown in FIG. 1 has two hardening stages. However, it is also feasible to use more than two such stages.

The thickness of the scattering films 19, 23 and the size of the collimator openings 29, 37 as well as the distance between the scattering films and the collimators 27, 35 are variable and can be matched to the energy spectrum of the ion/proton beam that enters the energy filter device.

The energy filter device 1 can be matched to the collimated beam 15, which is also referred to as the primary beam, by means of the thickness of the scattering films 19, 33 and the size of the collimator openings 29, 37.

FIG. 2 shows a second exemplary embodiment of an energy filter device 1', through which an ion beam 3 passes. In this case as well, it is assumed that a laser beam 5 which strikes a target, in this case a converter film 7, is used to produce a widely scattered ion beam with a broad spectrum, by forcing particles 9 (protons and heavy ions) out of the converter film 7.

A first collimator 11 with a collimator opening 13 is located at a distance from the converter film 7, through which collimator opening 13 a portion of the broadly scattered proton beam passes, thus resulting in a collimated beam 15. Underneath this beam, FIG. 2a shows the energy spectrum of this beam, while FIG. 2b shows the depth dose profile of this beam.

The production of the particle beam and its first collimation corresponds to the characteristics illustrated in FIG. 1.

The energy filter device 1' has a passive modulator 17', which comprises a magnetic filter 33 and an absorber 45.

The magnetic filter 33 has a homogeneous magnetic field and is formed, for example, by an electromagnetic dipole. The collimated beam 15 passes through the magnetic field, so that this results in a spectrally spread ion/proton beam 47. FIG. 2 shows the spread beam 47 in the form of a fan downwards, with high-energy particles having been deflected to a lesser extent by the magnetic field than particles with a lower energy level, and whose velocity is thus lower.

The absorber 45, which is wedge-shaped, is introduced into the profile of the spread beam 47 in such a way that the thicker part of the wedge is arranged at the top, and the thinner part at the bottom. The high-energy ions/protons thus pass through the thicker part of the absorber, and the low-energy ions/protons pass through its thinner part. The absorber is used for energy homogenization, and for increasing the transmission associated with this.

The angle of the walls 49a, 49b (which are arranged in the form of a wedge with respect to one another) of the absorber 45 can be matched to the desired energy loss, which is desired when the spread beam 47 passes through the absorber 45. It is also possible for the walls 49a and 49b, which in this case run in a straight line, that is to say lie on one plane, to be designed to be curved in a concave or convex shape, in order to influence the energy absorption in a specific manner.

By appropriate dimensioning of the absorber wedge, that is to say by the absorber 45 having a suitable thickness profile, it is thus possible to compensate for the different energy levels of the particles in the spread beam 47 by means of the different energy loss within the absorber, and thus to obtain a greatly improved range profile.

The absorber 45 is followed by a second collimator 51 with a collimator opening 53, which is used to filter out a desired energy band from the spread beam 47 which has passed through the absorber 45.

The beam which emerges through the collimator opening 53 is made parallel by means of a magnet 55 by forming a second magnetic field, with the opposite polarity to the first magnetic field.

After passing through the second magnetic field, this results in a beam 57 with a narrower energy range.

The energy spectrum of the spread beam 47 is illustrated underneath it in FIG. 2a, and its depth dose profile is illustrated in FIG. 2b. This clearly shows that the energy spectrum has a discrete high point, and thus that the depth dose profile has a relatively sharp maximum, a Bragg peak.

The second collimator 51 governs the upper and the lower energy limit of the beam 47a that is influenced by the absorber 45. The beams, which now effectively have a single energy state, are made parallel by the magnetic field of the magnet 55 of the passive modulator 17'. The parallel beam 57 which leaves the further magnet filter 45 is focused by a suitable lens, in this case, by way of example, a quadrupole pair 58. This results in a beam with a higher energy density.

The advantage of the wedge-shaped absorber 45 is its high transmission. The disadvantage is that the entire spectrum of the spread beam 47 is shifted towards lower energy levels. An energy filter device 1' of the type described here can be used to brake the intensity component of the radiation which is above a desired energy level to a desired energy level without any significant loss of intensity. If magnetic energy selection were to be carried out without a wedge-shaped absorber, thus by means of a collimator, the intensity component would be lost. A filter such as this would therefore have a poor transmission curve.

FIG. 3 shows a third exemplary embodiment of an energy filter device 1", through which an ion beam 3 passes.

In the case of the exemplary embodiment illustrated here, the ion beam is once again produced by means of a laser 5 which strikes a target, in this case a converter film 7, so that charged particles 9, that is to say protons of heavy ions, are forced out of this converter film 7. The converter film 7 is followed by a first collimator 11, which has a collimator opening 13 through which a collimated beam 15 passes, whose energy spectrum is illustrated in FIG. 3a, and whose depth dose profile is illustrated in FIG. 3b.

This beam is supplied to the energy filter device 1", which comprises a passive modulator 17". In the exemplary embodiment illustrated here, the modulator 17" has a non-linear filter, which has a first magnetic filter 59 and an apparatus 61 for clipping the intensity of the individual energy levels in the beam.

The magnetic filter 59 has a preferably homogeneous magnetic field, which spectrally spreads the collimated beam 15 passing through the magnetic filter 59. As is shown in FIG. 3, the collimated beam 15 is spread into a fan downwards, with high-energy particles, whose velocity is thus higher, being deflected less than low-energy particles in the spread beam 63, as in the case of the beam 47 shown in FIG. 2. The charged particles 9 are thus separated on the basis of their energy and velocity in the first homogeneous magnetic field of the magnetic filter 59.

The magnetic filter 59 is followed by a second collimator 65 with a collimator opening 67, which defines the upper and lower energy limits for the spread beam 63, thus resulting in a beam 69 being produced.

This beam 69 is made parallel by a magnet 71, with a second magnetic field, in the opposite direction to the first magnetic field, being used here, and the beam being deflected in the opposite direction to the direction produced in the first magnetic filter 59.

The parallel beam 73 which emerges from the magnet 71 thus has a narrower energy range than the spread beam 63. This parallel beam 73 is passed through the apparatus 61 for clipping the intensity of the individual energy levels, specifically through a selective collimator, so that the beam components which have been spatially separated on the basis of their energy are clipped to different extents, and a filtered beam 77 is produced.

FIG. 3C also shows a view of the selective collimator seen in the beam direction. This clearly shows the specially formed collimator opening 79, which is illustrated in the beam direction and has a broader free opening at the top than at the bottom. The collimator opening 79 effectively tapers in the form of a wedge downwards, in which case the profile of the opening can be influenced particularly well, especially by means of a multi-leaf collimator 85, in order to produce the desired opening contour.

A multi-leaf collimator 85 of the type mentioned here is illustrated in FIG. 4, with this figure showing a view of the collimator seen in the beam direction. The multi-leaf collimator 85 which is illustrated here is preferably in the form of a multi-leaf collimator and has two groups 87a and 87b (which are located alongside one another) of thin laminates 89a and 89b, which are arranged in pairs and can be adjusted by a motor.

FIG. 4 shows that the uppermost laminates of the right and the left group 87a and 87b have been moved towards one another, and that mutually facing ends are touching. Underneath the touching laminates, there is a group of laminates whose mutually facing ends are arranged at a distance from one another, with this distance decreasing from top to bottom. Finally, the lowermost laminates of the two groups 87a and 87b once again touch in the region of their mutually facing ends.

The thickness of the laminates, of which two mutually opposite laminates 89a and 89b are picked out here, is 2-4 mm.

The laminate depth measured at right angles to the image plane shown in FIG. 4, that is to say in the beam direction, is 5-10 cm, depending on the metal that is used for production of the laminates.

In the energy filter device 1" shown in FIG. 3, the beam 73 leaving the magnet 71 passes through the multi-leaf collimator 85. In the illustration shown in FIG. 4, the beam enters the image plane chosen here at right angles.

The distance between the upper laminates is greater than that between those located underneath. The width of the collimator opening 91 transversely with respect to the beam direction and transversely with respect to the deflection direction of the magnet 71 is greater for the high-energy component of the beam, which is deflected only slightly in the dipoles of the magnet 71, and becomes increasingly less for the low-energy component of the beam 73, which is deflected more strongly. The moving laminates 89a and 89b can be used to change the shape of the collimator opening 91, which in this case tapers from top to bottom, in order to predetermine the energy spectrum of the filtered beam 77 that is produced downstream from this special collimator. The spectrum of the beam 77 can be adapted individually by means of a multi-leaf collimator of the type mentioned here. It is thus possible to produce an energy spectrum which results in a depth dose profile with a high plateau (spread-out Bragg peak). This is shown underneath the beam 77 in FIGS. 3a and 3b.

The production of a beam such as this is medically highly advantageous.

The filtered beam 77 may be passed through a suitable lens, for example through a quadrupole pair 81, in order to obtain a filtered and focused beam 83.

FIG. 3a shows the energy spectrum of the filtered beam 77, and FIG. 3b shows its depth dose profile.

Various exemplary embodiments of energy filter devices are shown in FIGS. 1 to 3. These have different passive modulators. In the exemplary embodiments described here, one particular type of modulator has been used in each case. However, it is possible to combine the various modulators illustrated in FIGS. 1 to 3, and their elements, with one another in order to optimally harden the ion beam 3.

The energy filter device explained with reference to the figures is accordingly used for beams which have a broad spectrum with a relatively high low-energy component, such as those which result when ions are produced by pulsed laser beams. It is clearly evident that the modulators 17, 17' and 17" described in FIGS. 1 to 3 act as energy modulators and are used with the aim of hardening the energy spectrum of the beam, in order to produce a depth dose profile which can be used to good effect for ion beam therapy.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An energy filter device for beams which are used in the course of ion beam therapy, the filter device comprising a passive modulator which interacts with an incoming ion beam passing through the modulator to prevent the passage therethrough of low energy ions,
    wherein the modulator includes an absorber and a magnetic filter,
    wherein the absorber has a thicker area and a thinner area and is arranged such that relatively high-energy particles pass through the thicker area rather than relatively low energy particles;
    wherein the magnetic filter has a first magnetic field of a first polarity to deflect the incoming ion beam in a first direction and the modulator further includes a magnet with a second magnetic field with a second polarity opposite the first polarity of the first magnetic field of the magnetic filter to deflect the incoming ion beam in a second direction opposite the first direction.

2. The energy filter device as claimed in claim 1, wherein the absorber is positioned after the magnetic filter in the path of the ion beam.

3. The energy filter device as claimed in claim 2 wherein the magnetic filter has a homogenous magnetic field.

4. The energy filter device as claimed in claim 3, wherein the magnetic filter includes an electromagnetic dipole used to produce the magnetic field.

5. The energy filter device as claimed in claim 4, wherein the absorber has an inhomgenous thickness such that it is substantially wedge-shaped.

6. The energy filter device as claimed in claim 5, wherein the absorber further comprises entrance walls and exit walls positioned opposite to each other and including an acute angle, wherein the entrance walls and exit walls are substantially straight and are formed in an imaginary plane.

7. The energy filter device as claimed in claim 5, wherein the absorber further comprises entrance walls and exit walls positioned opposite to each other and including an acute angle, wherein the entrance walls and exit walls are curved in one of a convex shape and a concave shape.

8. The energy filter device as claimed in claim 1, further comprising a collimator positioned in front of the second magnet field in the path of the ion beam.

9. The energy filter device as claimed in claim 1, wherein the magnetic filter is a non-linear filter for separating the ion beam based on particle energy; and
    an apparatus for clipping the intensity of individual energy levels of ion beams.

10. The energy filter device as claimed in claim 9, wherein the magnetic filter has a homogenous magnetic field.

11. The energy filter device as claimed in claim 10, further comprising a collimator positioned in front of the magnet in the path of the ion beam.

12. The energy filter device as claimed in claim 11, wherein the apparatus for clipping the intensity of individual energy levels includes a select collimator with a variable collimator opening that is shaped such that a pass width of the more highly deflected beam components with a relatively high energy is greater than a pass width for less highly deflected relatively low-energy beam components.

13. The energy filter device as claimed in claim 12, wherein the select collimator is a multi-leaf collimator.

14. The energy filter device as claimed in claim 1, further comprising at least one additional passive modulator operable to cooperate with the passive modulator to prevent the passage of low energy ions.

15. An energy filter device for beams which are used in the course of ion beam therapy, the filter device comprising a passive modulator which interacts with an incoming ion beam passing through the modulator to prevent the passage therethrough of low energy ions,
    wherein the modulator includes a non-linear filter including a first magnetic filter for separation of the ion beam on the basis of the energy of particles in the ion beam, and
    an apparatus for clipping the intensity of individual energy levels of beams, where the first magnetic filter has a first magnetic field with a first polarity to deflect the ion beam in a first direction and the modulator includes a magnet with a second magnetic field with a second polarity opposite the first polarity to deflect the incoming ion beam in a second direction opposite the first direction.

16. The energy filter device as claimed in claim 15, further comprising a collimator positioned in front of the magnet in the path of the ion beam.

17. The energy filter device as claimed in claim 16, wherein the apparatus for clipping the intensity of individual energy levels includes a select collimator with a variable collimator opening that is shaped such that a pass width of more highly deflected beam components with a relatively high energy is greater than a pass width for less highly deflected relatively low energy beam components.

18. The energy filter device as claimed in claim 17, wherein the select collimator is a multi-leaf collimator.

* * * * *